US009370312B2

(12) United States Patent
Schwartz et al.

(10) Patent No.: US 9,370,312 B2
(45) Date of Patent: Jun. 21, 2016

(54) CORRELATION OF CARDIAC ELECTRICAL MAPS WITH BODY SURFACE MEASUREMENTS

(75) Inventors: Yitzhack Schwartz, Haifa (IL); Meir Bar-Tal, Zichron Ya'acov (IL); Joshua Porath, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1704 days.

(21) Appl. No.: 11/845,973

(22) Filed: Aug. 28, 2007

(65) Prior Publication Data

US 2008/0058657 A1    Mar. 6, 2008

Related U.S. Application Data

(60) Provisional application No. 60/824,680, filed on Sep. 6, 2006.

(51) Int. Cl.
*A61B 5/042* (2006.01)
*A61B 5/0408* (2006.01)
*A61B 5/053* (2006.01)
*A61B 5/00* (2006.01)
A61B 18/00 (2006.01)

(52) U.S. Cl.
CPC ........... *A61B 5/0422* (2013.01); *A61B 5/04085* (2013.01); *A61B 5/0538* (2013.01); *A61B 5/6805* (2013.01); *A61B 2018/00839* (2013.01)

(58) Field of Classification Search
CPC ............ A61B 5/04085; A61B 5/0422; A61B 5/6805; A61B 5/0538
USPC ........... 600/424, 425, 508, 523, 525; 607/122
See application file for complete search history.

(56) References Cited

U.S. PATENT DOCUMENTS

| 5,391,199 | A | 2/1995 | Ben-Haim |
| 5,471,982 | A | 12/1995 | Edwards et al. |
| 5,692,515 | A | 12/1997 | Rahn et al. |
| 6,226,542 | B1 | 5/2001 | Reisfeld |
| 6,301,496 | B1 | 10/2001 | Reisfeld |
| 6,584,343 | B1 | 6/2003 | Ransbury et al. |
| 6,625,482 | B1 * | 9/2003 | Panescu et al. ............... 600/424 |

(Continued)

FOREIGN PATENT DOCUMENTS

| JP | 8-322950 | 12/1996 |
| WO | WO 94/06349 | 3/1994 |

(Continued)

OTHER PUBLICATIONS

Huiskamp, G. et al 'A New Method for Myocardial Activation Imaging' IEEE Transactions on Biomedical Engineering vol. 44, No. 6 (1997) pp. 433-446.

(Continued)

*Primary Examiner* — Tammie K Heller
(74) *Attorney, Agent, or Firm* — Louis J. Capezzuto

(57) ABSTRACT

A reliable endocardial map is obtained by constructing a matrix relationship between a small number of endocardial points and a large number of external receiving points using a multi-electrode chest panel. Inversion of the matrix yields information allowing the endocardial map to be constructed. Subsequent maps are obtained noninvasively using the multi-electrode chest panel, applying new electrical signals to the matrix relationship, and again inverting the matrix to generate new endocardial electrical maps.

21 Claims, 9 Drawing Sheets

(56) References Cited

U.S. PATENT DOCUMENTS

| | | | |
|---|---|---|---|
| 6,650,927 B1 | 11/2003 | Keidar | |
| 6,772,004 B2 * | 8/2004 | Rudy | 600/509 |
| 6,892,091 B1 | 5/2005 | Ben-Haim et al. | |
| 6,975,900 B2 * | 12/2005 | Rudy et al. | 600/523 |
| 7,720,520 B2 * | 5/2010 | Willis | 600/424 |
| 7,957,784 B2 | 6/2011 | Voth et al. | |
| 2001/0056289 A1 | 12/2001 | Sippensgroenewegen | |
| 2002/0128565 A1 | 9/2002 | Rudy | |
| 2003/0120163 A1 | 6/2003 | Rudy et al. | |
| 2004/0006268 A1 * | 1/2004 | Gilboa et al. | 600/424 |
| 2004/0015194 A1 | 1/2004 | Ransbury et al. | |
| 2004/0068178 A1 | 4/2004 | Govari | |
| 2007/0060832 A1 | 3/2007 | Levin | |

FOREIGN PATENT DOCUMENTS

| | | |
|---|---|---|
| WO | WO 96/05768 | 2/1996 |
| WO | WO 97/24981 | 7/1997 |
| WO | WO 99/05962 | 2/1999 |

OTHER PUBLICATIONS

Gulrajani, R.M. 'The Forward and Inverse Problems of Electrocardiography' IEEE Engineering in Medicine and Biology Magazine vol. 17, No. 5 (1998) pp. 84-101.

Messinger-Rapport, B.J. et al 'The Inverse Problem in Electrocardiography: A Model Study of the Effects of Geometry and Conductivity Parameters on the Reconstruction of Epicardial Potentials' IEEE Transactions on Biomedical Engineering vol. BME-33, No. 7 (1986) pp. 667-676.

Puurtinen, H.G. et al 'Application of Lead Field Theory and Computerized Thorax Modeling for the ECG Inverse Problem' Proceedings of the $23^{rd}$ Annual International Conference of the IEEE Engineering in Medicine and Biology Society vol. 1 (2001) pp. 363-366.

Extended Search Report re: 07253530.5 dated Sep. 30, 2008.

Farina, D. et al. Optimization-Based Reconstruction of Depolarization of the Heart, Proc. Computers in Cardiology, Chicago, USA, 2004, 31, pp. 129-132.

Modre, Robert PhD et al. Atrial Noninvasive Activation Mapping of Paced Rhythm Data, J. Cardiocas. Electrophysiology 14:712-719, Jul. 2003.

Ramanathan, Charulatha et al. Noninvasive Electrocardiographic Imaging for Cardiac Electrophysiology and Arrhythmia, Nature Medicine, 2004, vol. 10, No. 4, pp. 422-428.

AU Examination Report AU2007216634 dated Jun. 4, 2012.
CA Examination Report CA2600208 dated Oct. 9, 2013.
CA Examination Report CA2600208 dated Nov. 21, 2014.
CN Office Action CN200710182138.8 dated Jun. 17, 2010.
CN Office Action CN200710182138.8 dated Jul. 30, 2010.
EP Examination Report EP07253530.5 dated Jul. 24, 2009.
EP Examination Report EP07253530.5 dated Nov. 22, 2013.
EP Examination Report EP07253530.5 dated Mar. 24, 2015.
JP Office Action JP2007-230556 dated Oct. 2, 2012.
U.S. Appl. No. 11/215,435 now abandoned.
U.S. Appl. No. 11/030,934 now U.S. Pat. No. 7,869,865.
U.S. Appl. No. 11/357,512 now U.S. Pat. No. 7,918,850.

* cited by examiner

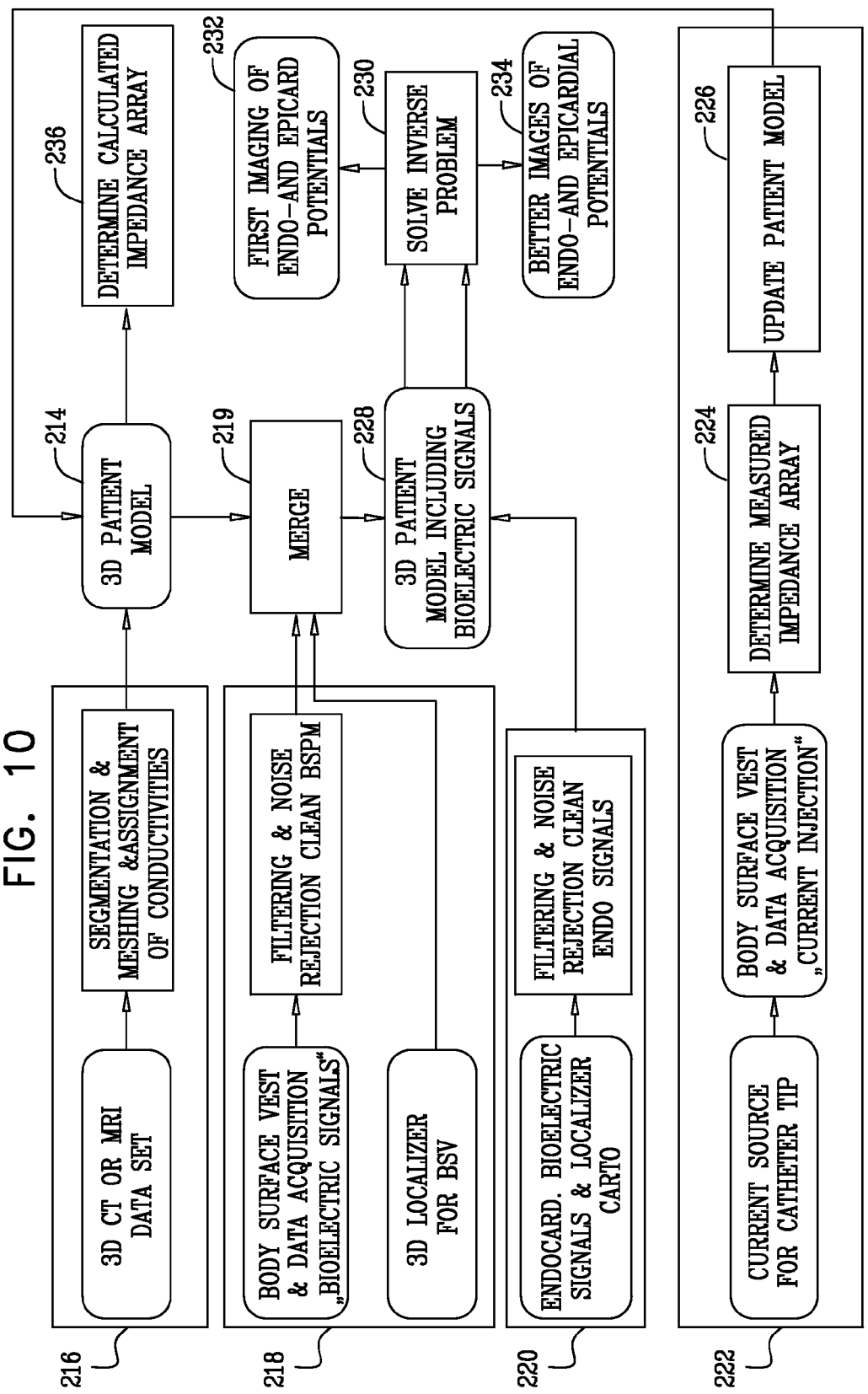

CORRELATION OF CARDIAC ELECTRICAL MAPS WITH BODY SURFACE MEASUREMENTS

CROSS-REFERENCE TO RELATED APPLICATIONS

This application claims the benefit of U.S. Provisional Application No. 60/824,680, filed Sep. 6, 2006, which is herein incorporated by reference.

BACKGROUND OF THE INVENTION

1. Field of the Invention

This invention relates to evaluation and treatment of cardiac arrhythmias. More particularly, this invention relates to improvements in electrical mapping of the heart for use in evaluation of cardiac arrhythmias and ablative therapy thereof.

2. Description of the Related Art

Methods are known for noninvasive mapping of electrical potentials in the heart based on body surface electrocardiographic (ECG) techniques. These methods combine 3-dimensional imaging with the ECG data in order to generate 3-dimensional maps of the electrical potentials on the epicardial surface, and on the endocardial surface, as well.

The document Modre et al., *Atrial Noninvasive Activation Mapping of Paced Rhythm Data*, J. Cardiovasc. Electrophysiology 14:712-719 (July 2003), describes a surface heart model activation time (AT) imaging approach, based on magnetic resonance imagine (MRI) and ECG mapping data. Both endocardial and epicardial surfaces might be mapped in this way. The AT pattern was compared to a CARTO™ map of atrial potentials. External anatomic markers were used to couple the CARTO data to the MRI coordinate system, by moving the catheter tip to marker locations at the body surface after internal mapping. It is proposed that AT imaging within the atria may be useful for noninvasive imaging of atrial activity in patients with focal arrhythmias.

SUMMARY OF THE INVENTION

In embodiments of the present invention, electrical maps of the heart are acquired by two modalities: one relatively more invasive and the other less invasive. In one embodiment, the more invasive map is an endocardial map acquired using a catheter mapping system. A plurality of less invasive maps may be acquired non-invasively, based on a body surface ECG. Alternatively or additionally, the less invasive maps may be acquired using an epicardial contact probe, such as a catheter inserted through the chest wall into the pericardium. The less invasive maps typically show electrical potentials on the epicardium, although they may also show endocardial potentials, as described in the above-noted document Modre et al. Less invasive maps are based on data acquired outside the heart, in which epicardial electrical potentials are primarily of interest, although they may incidentally include endocardial information.

The features of the endocardial and epicardial electrical maps may be registered with one another, using anatomical landmarks and/or electrical features of the maps. The purpose of registration is to establish a correspondence or correlation between the electrical features of the two maps. Once the correlation has been established, it is possible to apply an electrical transform function to subsequent, repeat epicardial maps to generate new versions of the endocardial map without necessarily repeating the invasive endocardial mapping procedure.

Aspects of the invention produce a patient-specific spatiotemporal map of endocardial electric potentials using a small number of endocardial measurements and a relatively large number of ECG channels, the latter obtained as a body surface potential map. In addition, spatiotemporal epicardial maps can be estimated.

For example, the method of the present invention may be used to follow up on ablation treatment of arrhythmias by non-invasive or pericardial approaches. After the treatment, it may be sufficient to repeat the acquisition of the epicardial map in order to determine whether the treatment was successful. The changes that are observed in the epicardial map may be projected onto the endocardial map in order to validate the treatment results.

The methods of the present invention may also be used in correlating endocardial and epicardial maps of other properties of the heart that can be measured and mapped in a similar fashion.

An embodiment of the invention provides a method for generating an electrical map of a heart of a living subject, which is carried out by inserting a probe, such as a catheter into a chamber of the heart. The probe has at least one electrode and may be provided with a first location sensor. Electrical signals are emitted from the at least one electrode from at least one transmission point within the heart, and received at least one receiving point. Typically, there are multiple transmitting points and receiving points. The receiving points may be internal or external to the subject. The method is further carried out by locating the receiving points relative to the transmission points, and calculating a functional relationship, such as a linear matrix relationship, between the emitted electrical signals and the received electrical signals. The calculation may be performed by determining a measured lead field matrix that defines a linear matrix relationship between the emitted electrical signals and the received electrical signals, and by calculating an inverted lead field matrix from the measured lead field matrix. Alternatively, the inverted lead field matrix can be determined without explicitly calculating measured lead field matrix. The method is further carried out by receiving electrophysiological signals at the same or other receiving points, and applying the inverted lead field matrix to the electrophysiological signals to obtain an endocardial electrical map.

In one aspect of the method the receiving points are located relative to the transmission points by associating the receiving points with a second location sensor, and reading the first location sensor and the second location sensor to determine differences therebetween.

According to still another aspect of the method, the catheter has at least two electrodes the electrical signals are emitted from different subsets of the electrodes. The emitted signals may be time or frequency multiplexed.

According to yet another aspect of the method, the electrode is a unipolar electrode Alternatively, the electrode may be bipolar.

In an aspect of the method impedances are determined between the receiving points and subsets of the transmission points.

In another aspect of the method signals are received from electrical dipoles that are generated among the subsets of the transmission points.

In still another aspect of the method emitting electrical signals, receiving the emitted electrical signals, determining a measured lead field matrix, and calculating an inverted lead field matrix are performed with respect to a predetermined phase of a respiratory cycle of the subject.

In a further aspect of the method emitting electrical signals, receiving the emitted electrical signals, determining a measured lead field matrix, and calculating an inverted lead field matrix are performed with respect to a predetermined phase of a cardiac cycle of the subject.

One aspect of the method includes acquiring a thoracic anatomic image, using the anatomic image to prepare a finite element model of the thorax and adjusting parameters of the finite element model to conform the calculated lead field matrix to the measured lead field matrix.

Yet another aspect of the method inverted lead field matrix is calculated by regularizing the measured lead field matrix. Regularization is achieved by removing a null space of the inverted lead field matrix.

Other aspects of the invention provide apparatus for carrying out the method.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein:

FIG. 10 is a functional block diagram of a method for developing a 3-dimensional patient-specific cardiac electroanatomic model in accordance with a disclosed embodiment of the invention.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Embodiment 1

Figure 1:
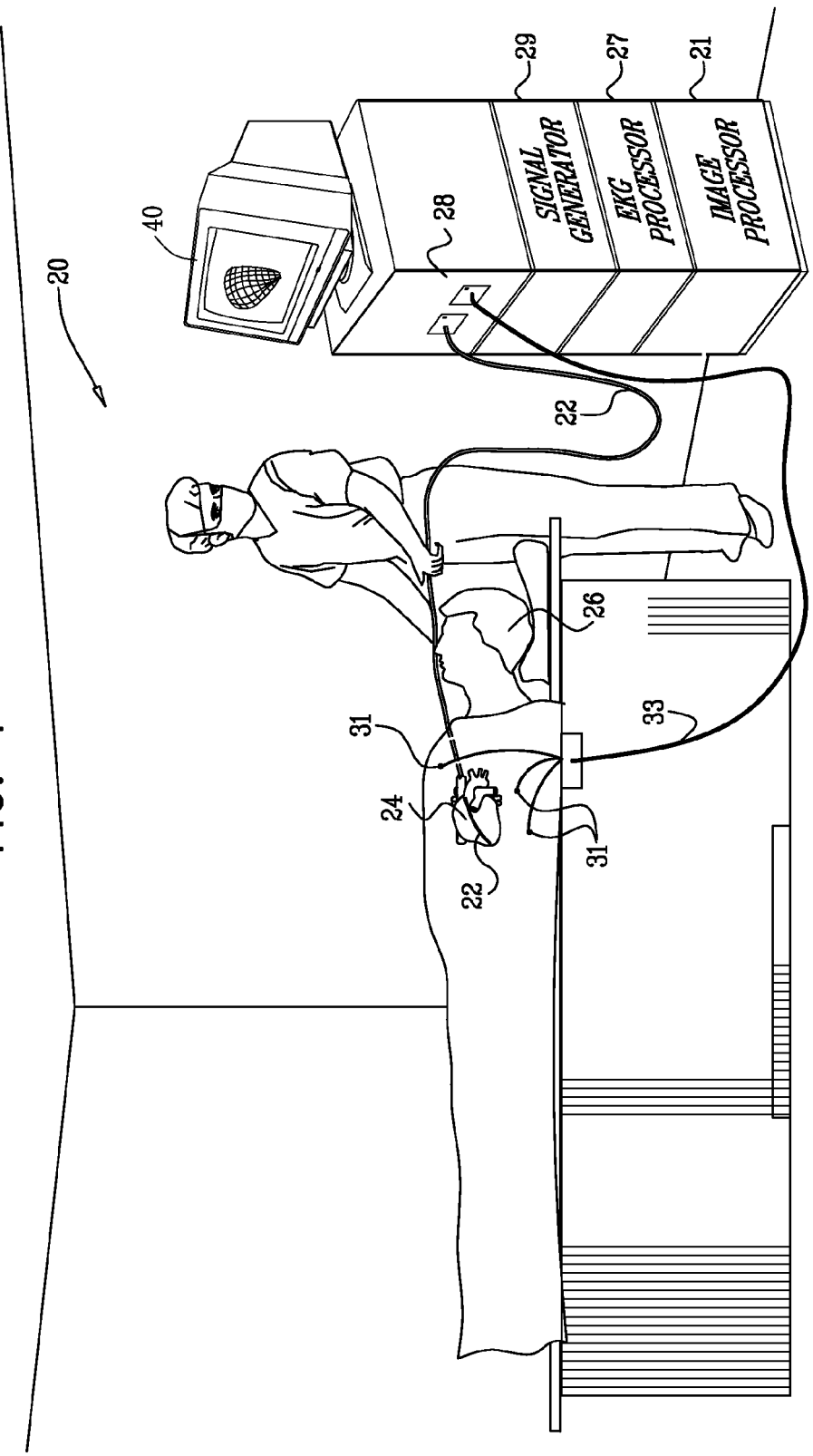
FIG. 1 is a high level diagram of a system for correlating a plurality of electrical cardiac maps, which is constructed and operative in accordance with a disclosed embodiment of the invention.

Turning now to the drawings, reference is initially made to FIG. 1, which is an illustration of a system 20, which is constructed and operative in accordance with a disclosed embodiment of the invention. The system 20 is used in determining the position of a probe or catheter 22, used for the acquisition of anatomic and electrical data, and for tissue ablation using the catheter 22. During acquisition of an endocardial electrical map, the catheter 22 is placed into chambers of a heart 24 of a subject 26 using a known intravascular approach. For obtaining an epicardial electrical map, the catheter 22 may be percutaneously inserted into the pericardial cavity that surrounds the heart 24. Alternatively, the epicardial electrical map may be obtained non-invasively, as described below in further detail. Exemplary methods and devices for cardiac mapping are described in U.S. Pat. Nos. 5,471,982, 5,391,199, 6,226,542, 6,301,496, and 6,892,091, and in PCT patent publications WO94/06349, WO96/05768 and WO97/24981, whose disclosures are incorporated herein by reference. U.S. Pat. No. 5,391,199, for example, describes a catheter including both electrodes for sensing cardiac electrical activity and miniature coils for determining the position of the catheter relative to an externally-applied magnetic field. Using this catheter, data can be collected from a set of sampled points within a short period of time by determining the electrical activity at a plurality of locations and determining the spatial coordinates of the locations.

Figure 2:
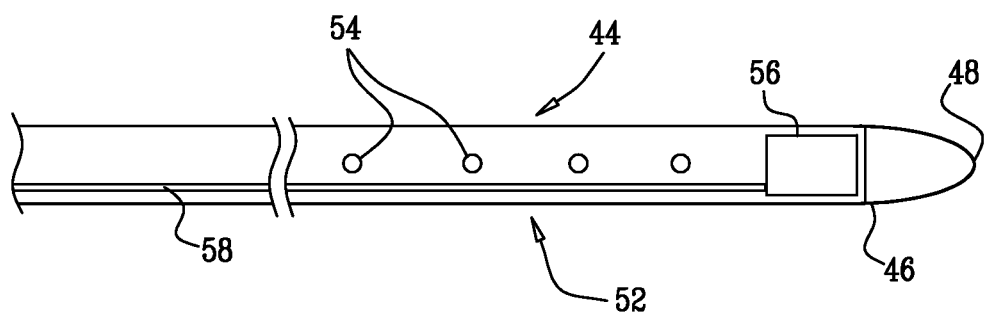
FIG. 2 is a plan view of the distal end of a catheter for use in the system shown in FIG. 1.

Reference is now made to FIG. 2, which is a plan view of a distal end 44 of an embodiment of the catheter 22 (FIG. 1). The distal end 44 includes an electrode 46 at its tip 48 for measuring the electrical properties of the heart tissue. The electrode 46 may be a unipolar or bipolar electrode. The electrode 46 is also useful for sending electrical signals to the heart for diagnostic purposes, e.g., for pace mapping, and/or for therapeutic purposes, e.g., for ablating defective cardiac tissue. The distal end 44 of the catheter 22 optionally includes an array 52 of non-contact electrodes 54 for measuring far field electrical signals. The array 52 is a linear array in that the non-contact electrodes 54 are linearly arranged along the longitudinal axis of the distal end 44. The distal end 44 of the catheter 22 further includes at least one location sensor 56 that generates signals used to determine at least the position of the catheter within the body. In some embodiments orientation of the catheter within the body also be determined. The location sensor 56 is preferably adjacent to the tip 48. This embodiment of the catheter 22 is described in further detail in the above-noted U.S. Pat. No. 6,892,091.

Referring again to FIG. 1, the electrodes and transducers of the distal end 44 of the catheter 22 are connected by a cable 58 through the insertion tube of the catheter 22 to a control processor 28 (FIG. 1), which controls other elements of the system 20, including a signal generator 29 for transmitting signal to the catheter 22, an image processor 21, and an EKG processor 27. The control processor 28 is shown for convenience as a single unit. However, it may be realized as a plurality of processing facilities for performing the diverse processing tasks described herein. The control processor 28 determines position coordinates of the catheter 22 relative to specific landmarks or features of the heart 24. The control processor 28 drives a display 40, which shows the catheter position inside the body and displays functional maps generated by the system. The control processor 28 also drives the ablation transducers that are located generally at the tip of the catheter 22. The catheter 22 is used in generating anatomic images or an endocardial electrical map. Additionally, the electrodes on the catheter may be used for ablation. The system 20 can be the CARTO™ XP EP Navigation and Ablation System, available from Biosense Webster, Inc., 3333 Diamond Canyon Road, Diamond Bar, Calif. 91765, U.S.A., suitably modified to embody certain features of the invention that are disclosed in further detail hereinbelow.

In some embodiments of the invention, epicardial electrical maps can be obtained noninvasively, using multiple body surface electrodes 31, of which three are shown representatively, it being known in the art that when using the noninvasive technique, much larger arrays of electrodes are typically required in order to obtain accurate epicardial electrical maps. The electrodes 31 may conveniently be mounted in multi-electrode chest panels as described in any of the following documents, all of which are herein incorporated by reference: Ransbury et al., U.S. Patent Application Publication No. 2004/0015194; Sippensgroenewegen, U.S. Patent Application Publication No. 2001/0056289; Ramanathan et al., in *Noninvasive Electrocardiographic Imaging for Cardiac Electrophysiology and Arrhythmia, Nature Medicine*, published on the Internet; and the above-noted document Modre et al. The electrodes 31 are connected to the control processor 28 by a cable 33, and linked to the EKG processor 27.

The electrodes 31 can alternatively be positioned internally within the subject. For example they could be esophageal leads or electrodes disposed, temporarily or permanently, within areas such as the coronary sinus or epicardium.

The above noted intrapericardial technique can be used to generate an epicardial electrical map. This method is still less invasive than the above-described intravascular catheterization technique for obtaining endocardial electrical maps. The technique employs an epicardial contact probe as the catheter 22, which is inserted through the chest wall into the pericardium, using known introduction techniques.

In either case, the epicardial electrical map typically shows the potentials on the epicardium, although it may also show endocardial potentials. Nevertheless, the term "epicardial electrical map" is employed herein, as the data of primary interest are obtained from outside the heart.

Using the image processor 21, which is linked with the display 40, the features of the endocardial and epicardial electrical maps are registered with one another, based on anatomical landmarks and/or electrical features of the maps. The purpose of this registration is to establish a transformation function, also referred to herein as a transform, between the electrical features of the two maps. Once the transform has been established, subsequently obtained epicardial electrical maps can be transformed into new versions of the endocardial electrical map. In some embodiments, the transform can be effected by a simple visual projection of the epicardial electrical map onto the endocardial electrical map. Alternatively, a mathematical transform may be applied to the new epicardial electrical maps in order to create new versions of the endocardial electrical map.

Suitable registration techniques used in one embodiment are disclosed in U.S. Pat. No. 6,650,927, of common assignee herewith, and herein incorporated by reference. The technique is briefly described:

The epicardial electrical map and the endocardial electrical map can be 3-dimensional maps. Registration of these maps can be performed using the methods disclosed in U.S. patent application Ser. No. 11/215,435, entitled "Segmentation and Registration of Multimodal Images using Physiological Data", of common assignee herewith, and herein incorporated by reference.

Embodiment 2

Figure 3:
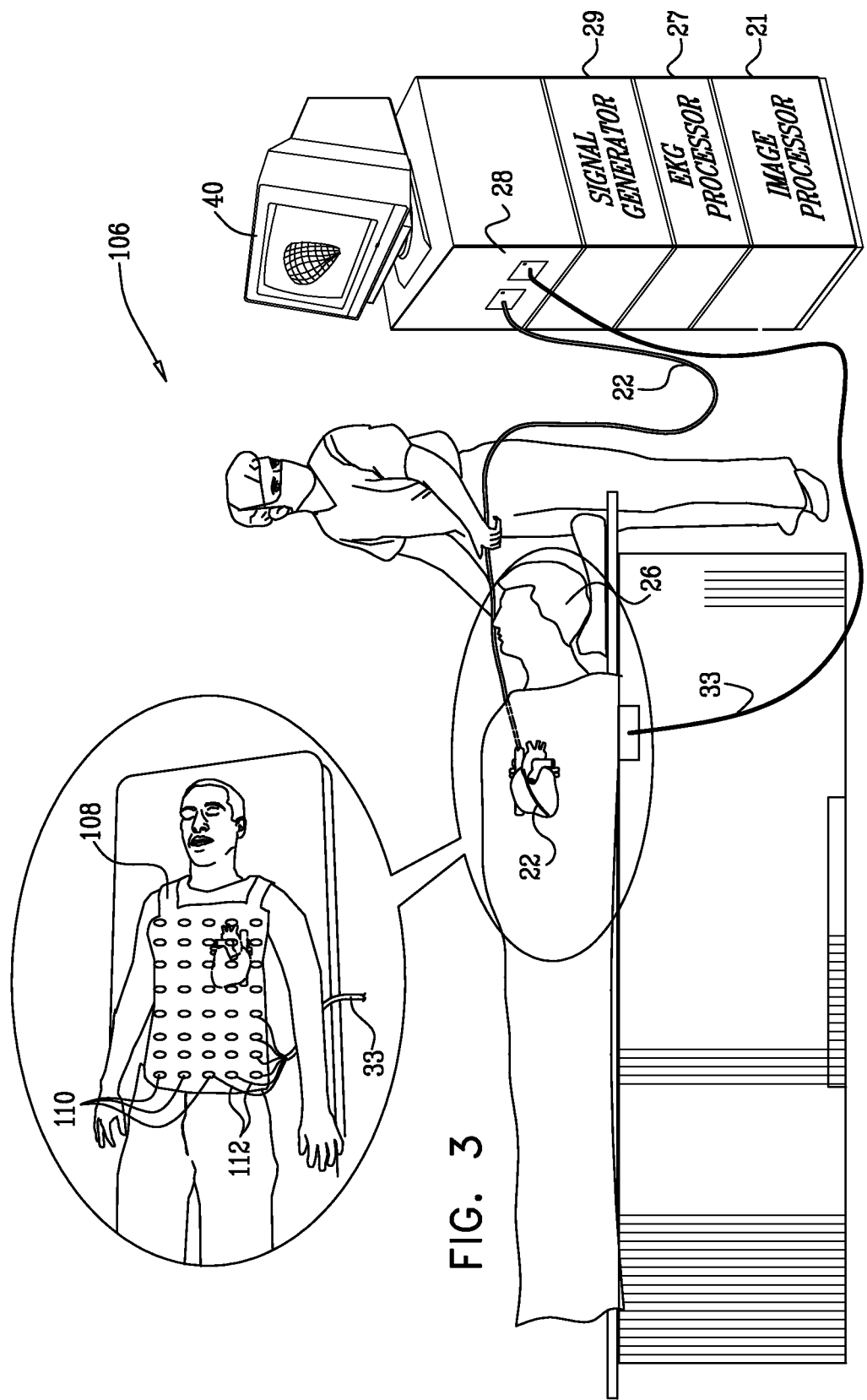
FIG. 3 is an illustration of a system for correlating endocardial and epicardial electrical maps, which is constructed and operative in accordance with an alternate embodiment of the invention.

Reference is now made to FIG. 3, which is an illustration of a system 106, which is constructed and operative in accordance with an embodiment of the invention. The system 106 is similar to the system 20 (FIG. 1). However the subject 26 is now clothed in a torso vest 108 that has a plurality of electrodes 110, typically between about 125 and 250 electrodes, which are disposed within the torso vest 108 to provide measurements of electrical potentials over the anterior, posterior and lateral aspects of the torso of the subject 26. The electrodes 110 are connected via leads 112 and the cable 33 to the control processor 28. The control processor 28 is modified for receiving and processing data from the torso vest 108.

The control processor 28 now contains electrical circuitry for impedance detection, as described in U.S. patent application Ser. No. 11/030,934, filed Jan. 7, 2005, which is assigned to the assignee of the present patent application and whose disclosure is incorporated herein by reference. The system is modified to generate, based on impedance measurements between a small number of endocardial points and the electrodes 110, a functional relationship therebetween. In one embodiment, this relationship is a linear multidimensional matrix of coefficients, referred to herein as a lead field matrix. The inverse of the matrix is then estimated, for example, as described in U.S. Patent Application Publication No. 2003/0120163 (Yoram Rudy et al.), whose disclosure is herein incorporated by reference. In this disclosure, the inverse matrix corresponds to epicardial electrical potentials. In the system 106, however, the inverse of the matrix corresponds to a map of endocardial conductances, which is an advance over prior techniques. In the past, it has not been possible to reliably evaluate the transfer function between external measurements and endocardial potentials. This is because the electrical field traverses fibromuscular tissue within the myocardium. As noted above, the amount and orientation of such tissue varies among individuals. Alternatively, in some embodiments of the system 106, the lead field matrix and its inverse may relate to a map based on epicardial conductances. Inversion of the lead field matrix is discussed in further detail below.

It is possible to use only one endocardial point. The receiving point or points can be internal or external to the subject. For example one or more esophageal leads coronary sinus electrodes, epicardial, or even intra-myocardial electrodes can be used as receiving points.

Figure 4:
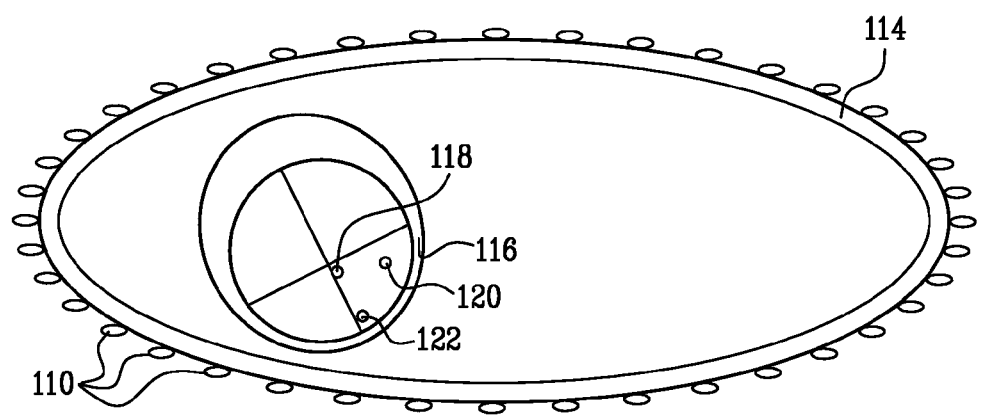
FIG. 4 is a simplified sectional view of a thorax showing a torso vest, and electrodes distributed about the thorax, in accordance with a disclosed embodiment of the invention.

Reference is now made to FIG. 4, which is a simplified sectional view of a thorax 114 showing the torso vest 108, and the electrodes 110 distributed about the thorax, in accordance with a disclosed embodiment of the invention. FIG. 4 also shows a right atrium 116, and includes three endocardial points 118, 120, 122. As explained below, impedance measurements are made between catheter electrodes positioned at the endocardial points 118, 120, 122 and the electrodes 110. In some applications, impedances are also measured between epicardially positioned electrodes (not shown in FIG. 4) and the electrodes 110.

Figure 5:
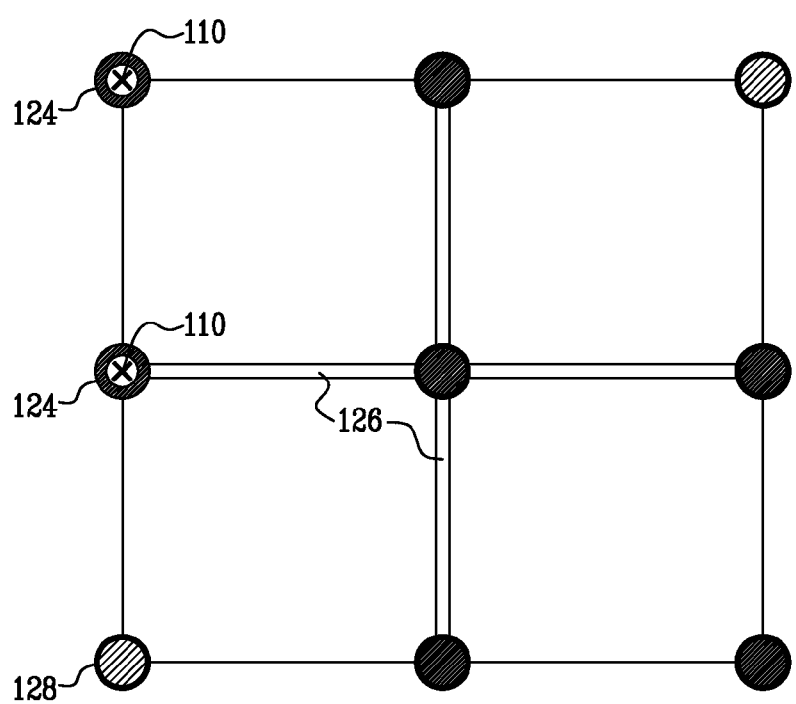
FIG. 5 is a schematic diagram illustrating details of the torso vest shown in FIG. 4, in accordance with a disclosed embodiment of the invention.

Reference is now made to FIG. 5, which is a schematic diagram illustrating details of the torso vest 108 (FIG. 3), in accordance with a disclosed embodiment of the invention. The torso vest 108 is constructed to include distributed stress points 124, which may coincide with the electrodes 110. However, such a coincidence is a matter of convenience, and is not essential. The stress points 124 are connected by flexible splines 126, having predetermined degrees of freedom. The splines 126 cause the torso vest 108 to closely conform to the geometry of the thorax 114 (FIG. 4). The torso vest 108 includes at least one location sensor 128, which is a reference point in a coordinate system that includes the electrodes 110. The use of such a location sensor is taught with reference to a locating system in commonly assigned U.S. Patent Application Publication No. 2004/0068178, whose disclosure is herein incorporated by reference. The location sensor 128 enables the positions of the electrodes 110 to be tracked during a medical procedure and to be related to intracardiac electrodes by difference computations. The location sensor 128 is not essential, so long as the electrodes 110 can be located relative to the endocardial points.

Figure 6:
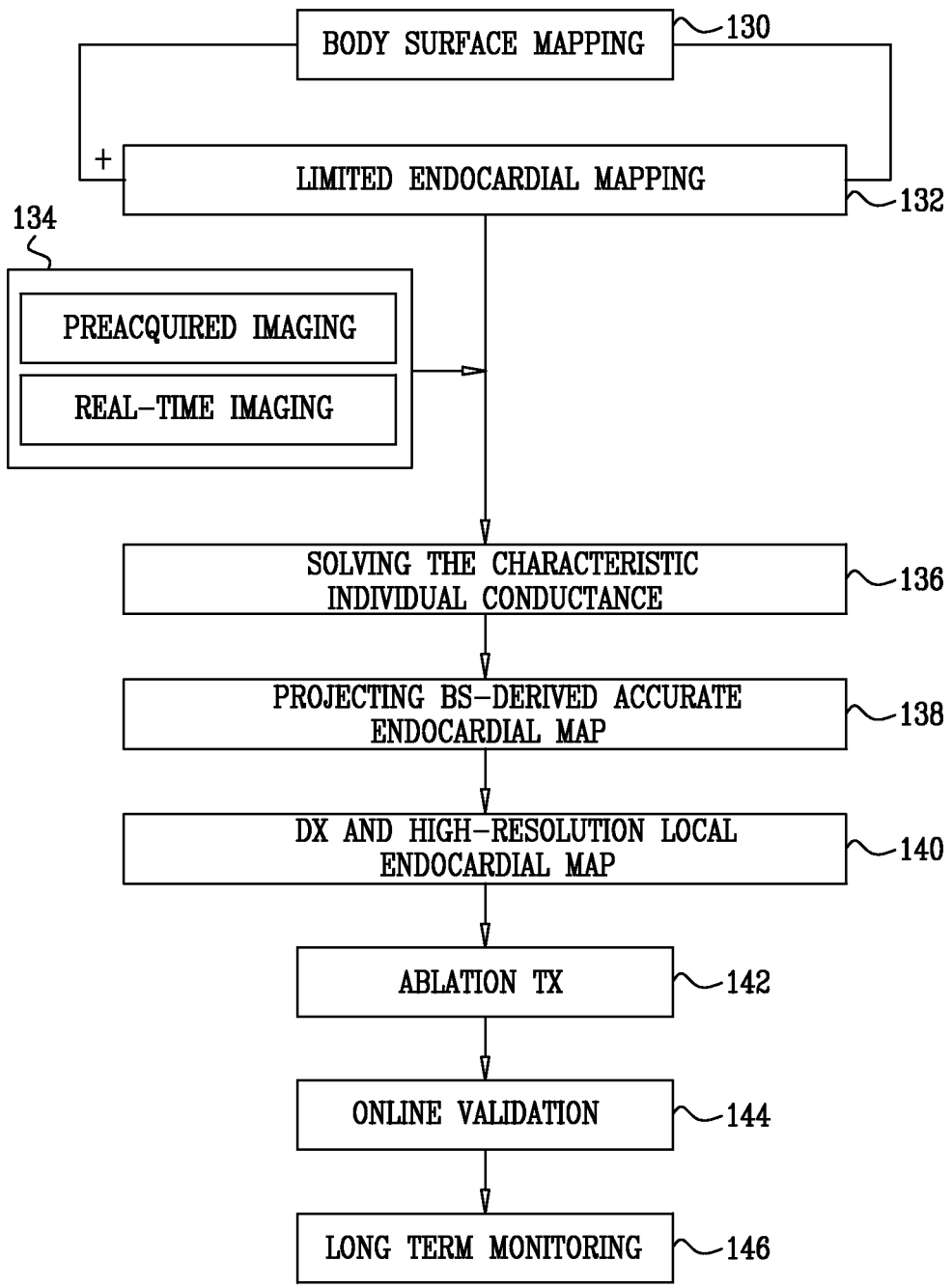
FIG. 6 is a flow chart of a method for correlating endocardial and epicardial maps, in accordance with an alternate embodiment of the invention.

Reference is now made to FIG. 6, which is a flow chart of a method for correlating endocardial and epicardial maps, in accordance with an alternate embodiment of the invention. The sequence of many of the process steps described in FIG. 6 is exemplary, and can be altered, as will be apparent to those skilled in the art.

At initial step 130 the subject is clothed in the torso vest 108, and connected to the control processor 28 (FIG. 3). A body surface epicardial electrical map is acquired as described in the above-noted U.S. Patent Application Publication No. 2003/0120163.

At step 132, the heart is catheterized, and a limited impedance map is acquired, again using the electrodes 110 on the torso vest 108 (FIG. 3). Typically, a small number of points, such as the endocardial points 118, 120, 122 (FIG. 4) are used to acquire the limited impedance map.

At step 134, an anatomic image of the heart is obtained. This can be preacquired, or obtained during the same session at which initial step 130 and step 132 are performed. Indeed, the acquisition of the anatomic image can optionally be obtained in near realtime, using known techniques, e.g., ultrasound imaging, if a patient wears a "vest" of body surface electrodes during computed tomographic (CT), myocardial perfusion SPECT. However, the impedance data acquired as described above may often be sufficient to develop a general body model, and to further evolve a patient-specific model from a general body model.

At step 136, applying the matrix solution techniques described in the above-noted U.S. Patent Application Publication No. 2003/0120163, conductances between the endocardial points 118, 120, 122 and each of the electrodes 110 (FIG. 3) are determined at different points in the cardiac cycle to generate the impedance map.

At step 138, the maps produced in initial step 130 and step 132 are combined and registered with the anatomic image obtained in step 134. This step transforms the body surface maps into a detailed combined endocardial map.

Step 140 is optional. In some applications, it is important to obtain segmental information regarding a cardiac chamber. In step 140, the maps are segmented to produce one or more regional maps. Image processing techniques for segmenting images and producing segmental data are well known in the art, and any suitable method may be employed for this step.

At step 142 ablative therapy on the heart is carried out conventionally. Then, at step 144 ablation is verified by obtaining a new detailed endocardial map by iterating the mappings and processing described in initial step 130 and steps 132, 136, 138. Techniques for assessing ablation are known, and are described, e.g., in commonly assigned U.S. patent application Ser. No. 11/357,512, entitled "Lesion Assessment by Pacing", whose disclosure is herein incorporated by reference.

At final step 146, at one or more times subsequent to the procedure detailed above, a new body surface epicardial electrical map is obtained as described in initial step 130. Then, using the same anatomic image and limited impedance maps that were obtained in steps 132, 134, one or more new combined endocardial maps are generated, for long term monitoring. The new maps can optionally be segmented, as noted above. While the electrodes of the vest will generally not coincide with their positions when the first electrical map was prepared, the procedure is nevertheless effective, so long as the relative positions of the vest electrodes with respect to the endocardial points can be determined.

General Operation

Figure 7:
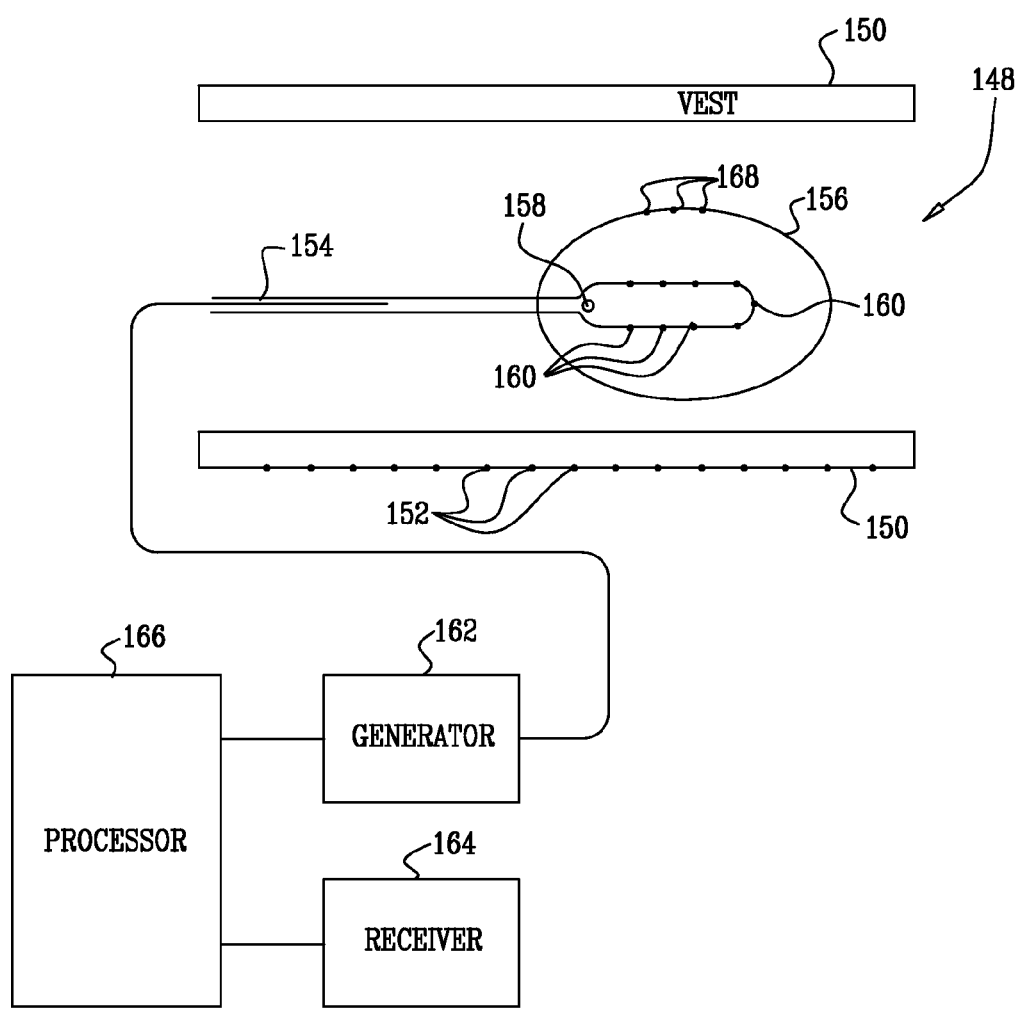
FIG. 7 is a schematic diagram illustrating aspects of a method of correlating endocardial and epicardial electrical maps, in accordance with a disclosed embodiment of the invention.

Reference is now made to FIG. 7, which is a schematic diagram illustrating further implementation details of the method described with reference to FIG. 6, in accordance with a disclosed embodiment of the invention. A sectional view of the thorax of a subject 148 is shown, enclothed in a multi-electrode chest panel 150 having electrodes 152. An intracardiac catheter 154 is in place within a cardiac chamber 156. The catheter 154 has a location sensor 158 and a plurality of electrodes 160. A generator 162 stimulates the electrodes 160. Signals are detected in the electrodes 152 and conducted to a receiver 164. A processor 166 linked to the receiver 164 then determines conductances between the chamber 156 and the electrodes 152 and produces a limited endocardial conductance map. It will be appreciated that relatively few electrodes 160, and hence relatively few intracardiac points are used to obtain the conductance or impedance measurements compared to the number of electrodes 152.

A matrix relationship can now be established between the signals emitted from points 168 on the endocardial surface of the chamber 156 and signals received by the electrodes 152. The precise respective locations of the points 168 are determined with reference to the location sensor 158 during the catheterization procedure. By inverting the matrix, using the various techniques disclosed below and in the above-noted document Rudy et al., it is possible to calculate potentials within the chamber 156 at the points 168, once the signals at the electrodes 152 are known. By performing this calculation at different times during the cardiac cycle and the respiratory cycle, and again, after withdrawal of the catheter, a time-varying endocardial electrical map of the chamber 156 can be generated. This map can be regenerated in future sessions simply by measuring electrical signals in the multi-electrode chest panel and applying them as coefficients of the same adjusted matrix, and repeating the matrix inversion, or applying them directly to the previously inverted matrix.

This method thus involves an integration of information from the tip of the catheter. First, measured endocardial potentials are added to elements of the lead field matrix, sometimes referred to as a "measured lead field matrix". Second, the lead field matrix is updated using impedance measurements taken between the tip of the catheter and the electrodes of the vest. As the catheter is moved, its position being tracked continuously, more measurements are accumulated both for the endocardial potential and for the lead field matrix. These measurements are used to progressively improve inverse solutions for the lead field matrix.

Establishing a reliable linear matrix relationship between the signals emitted from points 168 on the endocardial surface of the chamber 156 and signals received by the electrodes 152 is essential to obtain a competent endocardial (or epicardial) electrical map that can be regenerated from time to time and compared with previous instances. This problem, known as the "inverse problem", is known to be complicated in the sense that a spatial ambiguity inherently exists. In the past, mathematical procedures that were applied to endocardial potentials tended to produce poor image resolution. While solving the inverse problem using epicardial potentials delivers reasonable results, application to the endocardium leads to smeared out images. The problem is further complicated by the fibrous structure of the cardiac muscle, which varies among patients. Dealing with this requires a tensor-impedance model, which cannot easily be estimated from the MRI or CT scans.

The Forward Problem

The "forward problem" is the process of finding electric potentials in a medium with given electric and dielectric characteristics (conductivities) for a given distribution of electrical sources. This problem leads to a linear matrix equation with a unique solution:

$$A \cdot \vec{x} = \vec{b} \qquad (1),$$

where A is the transfer matrix (lead field matrix), $\vec{x}$ are current sources or endocardial and epicardial potentials or transmembrane potentials, and $\vec{b}$ is an array of electric potentials measured at the body surface vest, i.e., a body surface potential map.

Model Based Approach

In one approach, general human tissue conductivities and segmentation of the MR/CT model are characterized. The lead field matrix is calculated using a Finite Element Method (FEM) solver. A mechanical or electrical model has some freedom to represent the key factors ($\vec{p}$) that affect the matrix A, i.e., $$A = A(\vec{p}) \qquad (2).$$

The key factors ($\vec{p}$) can be the geometrical position or size of organs and the proportion of various tissues within the field of observation. Conductivities of organs and tissues differ among individual patients. For example, fiber direction affects the direction of the conductivity tensor in the myocardium. The model is improved and made patient-specific by characterizing these differences, which are reflected in the lead field matrix.

Measurements made by the injected signals are used to optimize the key factors ($\vec{p}$), so that the FEM solution becomes:

$$\hat{p} = \underset{\vec{p}}{\arg\text{Min}} \sum \left\| \vec{b}_c - Z_{\vec{r}}(\vec{p}) v_{\vec{r}} \right\|^2. \qquad (3)$$

where: $v_{\vec{r}}$ is the current injected into the catheter, placed at position $\vec{r}$ (in the reference coordinate system, grounded at that time). $Z_{\vec{r}}(\vec{p})$ is the impedance matrix calculated by the FEM solver for the point sources $v_{\vec{r}}$. For a set of mechanical or electrical model parameters ($\vec{p}$), the values $\vec{b}_c$, are a vector indicating the measured voltages in the set of receiving locations. The measurements may be impedance measurements. Alternatively, they may be measurements of the lead field matrix based on signals from electrical dipoles. Such dipoles may be generated by establishing a voltage difference between two adjacent electrodes in a catheter. A dipole can be directed in the three orthogonal directions if the electrodes are suitably arranged.

Optimizations for measured impedance ($\vec{z}$) are given by Equation 4.

$$\hat{p} = \arg\text{Min}\Sigma \| \vec{z}_{measured} - \vec{z}_{calculated}(\vec{p}) \|^2 \qquad (4).$$

Choices for the set of parameters ($\vec{p}$) include organ size, conductivity, fiber direction, and anisotropy ratio. Known optimization search algorithms can be used to determine values for the set of parameters ($\vec{p}$), e.g., genetic algorithms, simulated annealing, and neural networks, or hybrids thereof. Examples of such optimizations are disclosed in D. Farina, O. Skipa, C. Kaltwasser, O. Dössel, and W. R. Bauer, "Optimization-based reconstruction of depolarization of the heart," Proc. Computers in Cardiology, Chicago, USA, 2004, 31, 129-132.

Dipole generated potentials act the same as a monovoltage source when applied to the lead field matrix. In some cases, it is more convenient to describe cardiac electrical activity as a set of dipoles spread over the myocardium in which intensity and directional parameters vary over the cardiac cycle.

Using the set of parameters ($\vec{p}$), one can calibrate the FEM model in order to represent the patient's anatomy accurately. Generating a signal from inside the heart gives important information concerning the myocardial properties, namely correctness of assumptions on fiber direction. The signal can reveal other diagnostic information as well. Ischemic, scar and stent-related tissue may have significant deviations from normal conductivity. An added benefit of this approach is a visual map of myocardial impedance, which may itself have diagnostic value. Additionally or alternatively, the catheter may be placed epicardially, and the method of signal injection applied to epicardial leads. When the procedure is performed in this manner, it is possible to generate epicardial electrical maps of the heart based on external readings. The discussion that follows is directed to endocardial maps, but is applicable, mutatis mutandis, to epicardial map generation. If desired, the principles disclosed herein can be applied to establish transform matrices relating epicardial potentials to endocardial signals.

Alternatively, current can be injected through two neighboring intracardiac electrodes, thus mimicking a current dipole. In this way, some matrix elements of the lead field matrix A can be measured directly. This procedure can be used to update the original lead field matrix, or it can be used to construct the lead field matrix A without any MRI or CT data set. In either case, a body surface potential map (BSPM) is generated using signals using injected currents instead of current dipoles arising from bioelectric sources.

The mathematical solution to the inverse problem is degraded by respiration. This can be minimized by gating data collection at one point in the respiratory cycle, e.g., end expiration. However, it may be desirable to data throughout the respiratory cycle, and constructing a respiration dependent lead field matrix that is corrected for the phase of the respiratory cycle. The quality of the solution to the inverse problem improves considerably when this is done.

The inventors have discovered how to overcome technical difficulties inherent in the matrix inversion. By injecting signals in different combinations, typically in a relatively few sources located in the cardiac chamber, and measuring the signals at receiving points, the lead field matrix can be determined accurately, column-by-column. The calculation is iterated using as many different combinations of intracardiac electrodes as there are unknown coefficients in the matrix. Of course, the number of coefficients depends on the numbers of intracardiac sources and external leads.

If a multi-electrode catheter, e.g., the PENTARAY™ High-Density Mapping Catheter, available from Biosense Webster, Inc., is used, endocardial potentials are measured at many points while the catheter is stationary. This allows the torso vest measurements to be rapidly completed.

Figure 8:
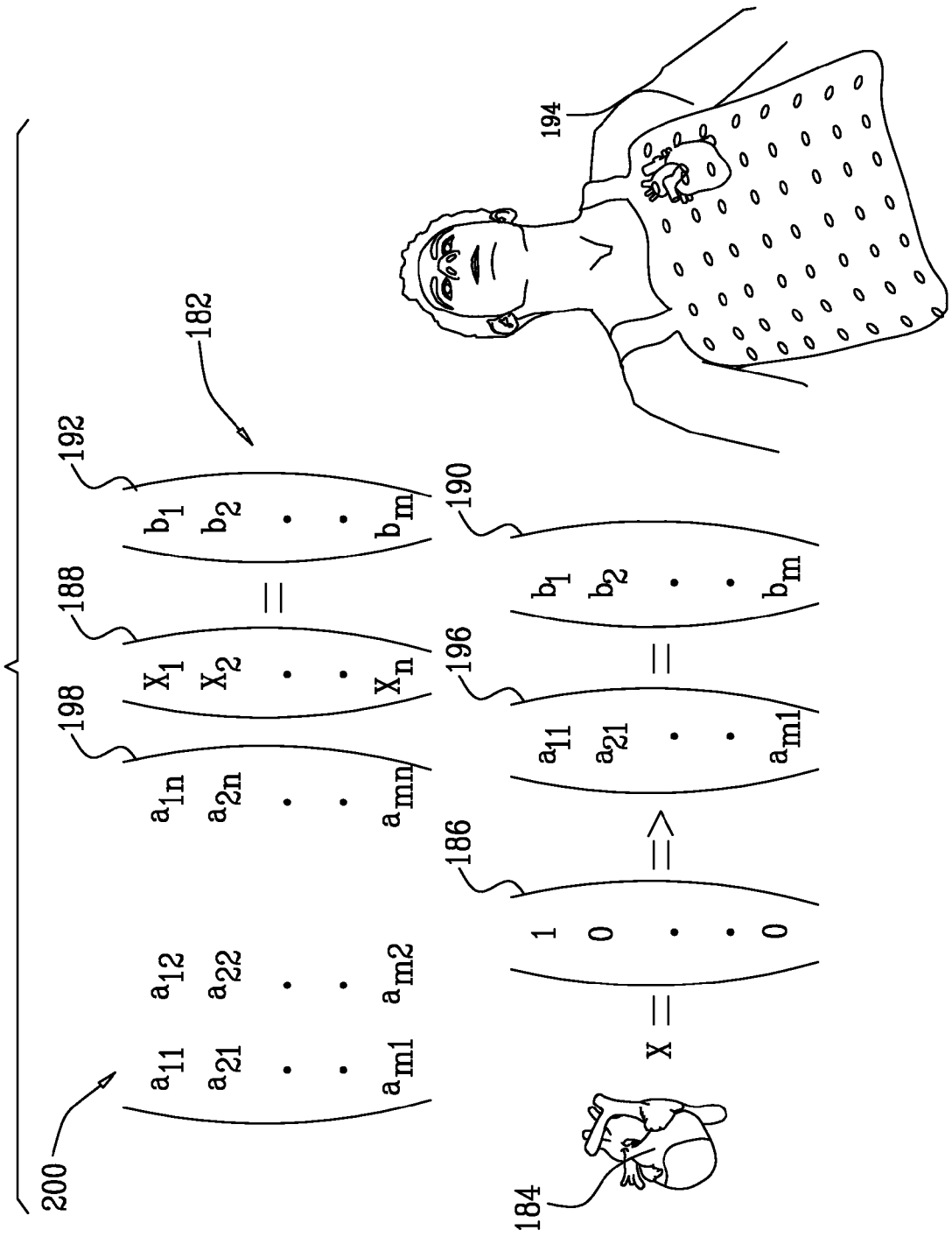
FIG. 8 is a diagram illustrating a technique for solving a forward matrix problem in accordance with a disclosed embodiment of the invention.

Reference is now made to FIG. 8, which is a diagram illustrating a technique for developing a forward matrix in accordance with a disclosed embodiment of the invention. Equation 1 is illustrated in a matrix form 182 in the upper portion of FIG. 8. An electrical signal is injected, using two or more sources inside a chamber of heart 184, e.g., electrodes 160 (FIG. 7). As illustrated in the lower portion of the FIG. 8, this signal is represented as a vector 186, corresponding to vector 188 in the upper portion of the figure. An plurality of impedance measurements, represented as vector 190 and corresponding to vector 192 in the upper portion of the figure, are taken between the sources and a plurality of external leads on torso 194, e.g., electrodes 152 (FIG. 7). This allows one column 196 of lead field matrix 198 to be established. In the example of FIG. 8, the column 196 is the leftmost column 200 of the lead field matrix 198. By iteratively changing the location of the source signals or, in the case of a multi-element mapping catheter, varying the combination of source signals, a matrix equation is created and solved. At the same time, the coefficients of the lead field matrix 198 are determined with great accuracy, noise being swamped out by the relatively large magnitude of the injected signals.

Figure 9:
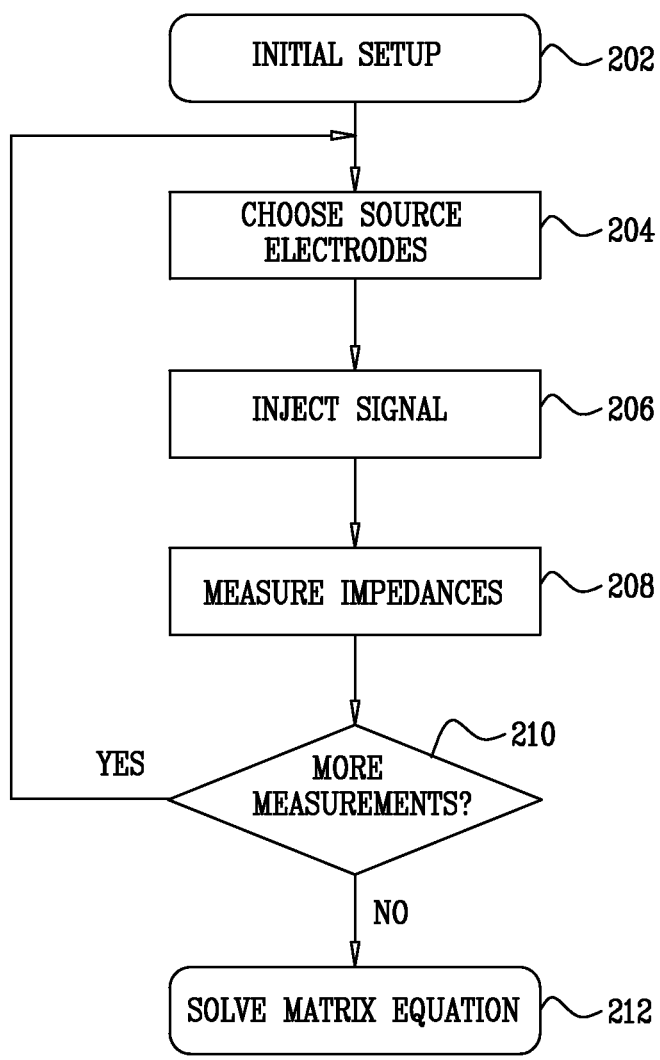
FIG. 9 is a flow chart of a method for determining a lead field matrix by signal injection in accordance with a disclosed embodiment of the invention.

Reference is now made to FIG. 9, which is a flow chart illustrating the above-described method for determining a measured lead field matrix by signal injection in accordance with a disclosed embodiment of the invention. At initial step 202 the patient is prepared by applying a torso vest and inserting a cardiac mapping catheter linked to a location processor, e.g., the system 106 (FIG. 3). It is desirable that the mapping catheter has multiple electrodes. This expedites the procedure as sufficient sources can be used without excessive navigation of the catheter within the heart. The number of measurements required to be taken in order to determine the lead field matrix is recorded.

Next, at step 204 a combination of at least two intracardiac source leads is chosen. The locations of these sources with respect to reference features of the cardiac anatomy are known accurately by virtue of the location processing facilities of the system 106.

It is also possible to employ unipolar leads in step 204, with appropriate adjustment in the computation of the lead field matrix as will be apparent to those skilled in the art.

Next, at step 206 an electrical signal is injected using the current source leads to create an electrical dipole. Suitable values for this signal are 1-10 mA at 1-100 kHz. The signals may be constant voltage or constant current signals.

Next, at step 208 impedance measurements are recorded between the source leads chosen in step 206 and each of the leads of the torso vest. Impedances may be measured using the teachings of commonly assigned U.S. Patent Application Publication No. 2007/0060832, entitled "Detection of Skin Impedance", which is incorporated herein by reference. In embodiments employing electrical dipoles, the dipole position and orientation are determined at the torso vest leads.

Control now proceeds to decision step 210, where it is determined if more measurements are required. If the determination at decision step 210 is affirmative, then control returns to step 204 to select another source.

If the determination at decision step 210 is negative, then control proceeds to final step 212. The matrix equation is solved and the lead field matrix values reported.

As noted above the measurements described in FIG. 8 and FIG. 9 are gated with respect to the respiratory cycle. In addition, they are gated with respect to the cardiac cycle. By repeating the measurements at different points in the cycles, a time-varying patient-specific set of lead field matrices can be obtained at any desired spatiotemporal resolution.

It will be recalled from consideration of the finite element model that parameter optimization is necessary. After performing final step 212, and once a reliable lead field matrix is available, the optimization algorithm can be applied to establish the parameters ($\vec{p}$) in Equation 3 in conformity with the actual lead field matrix with greatly reduced modeling errors in the resulting patient-specific finite element model. The solution of the inverse problem can then be developed with far greater confidence. Ultimately, near-perfect images depicting the electrophysiology in a patient's heart can be produced from a few initial intracardiac measurements without artifacts caused by the respiratory cycle. These "4-D" images can be repeated from time to time, for example to evaluate therapy. It should be noted that the receiving points in subsequent sessions need not be identical to those in the original session, only that their relative locations with respect to the original transmission points or original receiving points be identifiable, for example by reference coordinates. Application of inverted lead field matrix to the new receiving points remains valid.

Embodiment 3

$$\hat{p} = \underset{\vec{p}}{\arg\min} \sum \left\| Z_{\vec{r}}^{-1}(\vec{p})\vec{b}_c - v_{\vec{r}} \right\|^2. \tag{5}$$

The notation in Equation 5 is the same as for Equation 4. The model-based optimization techniques described by Equation 4, are now applied to directly determine the inverted lead field matrix $Z_{\vec{r}}^{-1}$ without explicitly calculating the lead field matrix itself.

Embodiment 4

Reference is now made to FIG. 10, which is a functional block diagram of a method for developing a 3-dimensional patient-specific cardiac electroanatomic model in accordance with a disclosed embodiment of the invention. The functional diagram can be implemented by specialization of the system 106 (FIG. 3) and employing the techniques and apparatus disclosed above with reference to Embodiments 1, 2, 3, and using the method described with reference to FIG. 9.

Initially a 3-dimensional anatomical patient 25 model 214 is prepared in functional group 216 using conventional 3-dimensional anatomic imaging modalities, This is similar to step 134 (FIG. 6), but usually extends to the thoracic organs and tissues beyond the heart itself. Functional group 218 develops a matrix of electrical signals having known coordinates in the subject's body, which is merged in functional block 219 with the model 214.

In functional group 220 An electroanatomical map is generated during cardiac catheterization as described in Embodiment 1. This map may be obtained using the CARTO XP EP Navigation and Ablation System, available from Biosense Webster Inc., 3333 Diamond Canyon Road Diamond Bar, Calif. 91765.

During the catheterization, in functional group 222 the method described with reference to FIG. 9 is applied. A measured impedance array is computed in functional block 224. The array is applied in block 226. This array is used to improve the model 214 of functional block 226, and thus contributes to a model 228. The model 228 is then used to solve the inverse problem and optimize FEM parameters (Equations 3, 4, 5) in functional block 230. Typically, the inverse problem, described below, may be solved initially in block 230, prior to the contribution of data via functional group 222, and initial electro-anatomical images are produced in functional block 232. In the initial solution, a preliminary set of electroanatomic images of endocardial potentials and optionally epicardial potentials may be developed in functional block 232. Subsequently, after including the benefits of functional group 222, improved images are generated in functional block 234. Another effect of the data provided by functional group 222 is the computation of a lead field matrix in functional block 236. This may be iteratively compared to the matrix measured in functional block 224 and applied to improve the FEM using the optimization algorithm for solving Equations 3, 4, 5.

The system operation described in FIG. 10 can be used to determine the dependency of the lead field matrix on motion during cardiac cycle cc(t) by determining respiratory parameters r(t). The technique ultimately speeds up catheterization procedures, improves the diagnosis of arrhythmias and infarctions, and improves the outcome of cardiac interventional therapies.

The Inverse Problem

A major objective, using the method and systems described in FIG. 6 and FIG. 7, is calculation of electrical sources in the endocardium based on a few endocardial potentials and many body surface measurements, which is known as the "inverse problem". In Equation 1, the vector of measured signals $\vec{b}$ is known. As noted above, the lead field matrix A may be calculated by solving several forward calculations using MRI or CT scans of the patient. Then the vector $\vec{x}$, describing the sources, is to be determined from:

$$A^{-1} \cdot \vec{b} = \vec{x} \qquad (6).$$

Mathematically, it is necessary to find the inverse $A^{-1}$ of the lead field matrix A. Unfortunately this problem is ill-posed. The matrix A has a non-vanishing null-space, i.e., different vectors $\vec{x}$ can be found, that belong to this null-space and lead to potentials $\vec{x}$ smaller than noise. Every linear combination of a vector $\vec{x}$ with vectors out of the null-space leads to the same potentials $\vec{b}$ and is therefore a solution of Equation 1. Moreover, the coefficients of the matrix A bear some uncertainty due to the unknown individual conductivities.

Solution by Regularization

Regularization is a well-described approach to the inverse problem in which the null space of the inversion is discarded. The most commonly used method is Tikhonov regularization with a Tikhonov new factor of zero that selects the solution with the smallest norm (smallest possible source).

There are two major factors that improve the quality of inversion when the lead field matrix is determined according to the methods described above. First, the signal-to-noise ratio is improved due to the magnitude of the injected signal. ECG transmembrane potentials are on the order of 10 mV and relatively short in duration, while the generated signal is on the order of volts and much longer in duration. Thus, averaging techniques can be used to further improve the signal-to-noise ratio. Improvements of two orders of magnitude are easily achieved. This allows less energetic eigenvalues to participate meaningfully in the solution, and ultimately improves reliability of the endocardial potentials observed. Second, the quality of the matrix improves as larger numbers of intracardiac sources are employed. To this end, the use of a multi-element mapping catheter is desirable and a torso vest having large numbers of receiving electrodes.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for generating an endocardial electrical map of a heart of a living subject, comprising the steps of:
   using a torso vest on an exterior of the subject located at a thorax of the subject, the torso vest having a plurality of electrodes distributed thereon;
   inserting a catheter into a chamber of the heart using an intravascular approach, said catheter having at least one electrode;
   injecting electrical signals from said at least one electrode of the catheter from at least one transmission point within the heart by gating to one point in the respiratory cycle;
   receiving said injected electrical signals in at least one receiving point on the torso vest that is gated to the one point in the respiratory cycle;
   locating said at least one receiving point relative to said at least one transmission point;
   determining a functional relationship between said injected electrical signals and said received electrical signals as a measured inverted lead field matrix based on impedance between the at least one electrode of the catheter from at least one transmission point within the heart and the at least one receiving point on the torso vest at different times during a cardiac cycle and a respiratory cycle;
   receiving electrophysiological signals at a receiving point on the torso vest other than the at least one receiving point; and
   applying said functional relationship to said electrophysiological signals and generating a time-varying endocardial electrical map that is without artifacts caused by the respiratory cycle due to the gating to the one point in the respiratory cycle.

2. The method according to claim 1, further comprising the steps of:
   acquiring an anatomic image of a thorax of said subject;
   using said anatomic image, preparing a finite element model of said thorax having parameters, said finite element model having a calculated inverted lead field matrix; and
   adjusting said parameters to conform said calculated inverted lead field matrix to said measured inverted lead field matrix.

3. The method according to claim 1, further comprising the step of withdrawing said catheter from said subject prior to performing said steps of receiving electrophysiological signals and applying said functional relationship.

4. The method according to claim 1, wherein said at least one receiving point is external to said subject.

5. The method according to claim 1, wherein said catheter has at least two electrodes and wherein said injecting electrical signals step is performed by time multiplexing said electrical signals using different subsets of said electrodes.

6. The method according to claim 1, wherein said catheter has at least two electrodes and the electrical signals are injected by frequency multiplexing said electrical signals using different subsets of said electrodes.

7. The method according to claim 1, wherein said at least one electrode is a unipolar electrode.

8. The method according to claim 1, wherein said at least one electrode is a bipolar electrode.

9. The method according to claim 1, wherein said steps of injecting electrical signals, receiving said injected electrical signals, and determining a functional relationship are performed with respect to a predetermined phase of a respiratory cycle of said subject.

10. The method according to claim 1, wherein said steps of injecting electrical signals, receiving said injected electrical signals, and determining a functional relationship, are performed with respect to a predetermined phase of a cardiac cycle of said subject.

11. A method for generating an endocardial electrical map of a heart of a living subject, comprising the steps of:
    using a torso vest on an exterior of the subject located at a thorax of the subject, the torso vest having a plurality of electrodes distributed thereon;
    inserting a catheter into a chamber of the heart using an intravascular approach, said catheter having a first location sensor and at least one electrode, the first location sensor being used to determine position coordinates of the catheter within the chamber of the heart;
    injecting electrical signals from said at least one electrode of the catheter at a plurality of transmission points within the heart by gating to one point in the respiratory cycle;
    receiving said injected electrical signals at a plurality of receiving points that are on the torso vest external to said subject that is gated to the one point in the respiratory cycle;
    locating said receiving points relative to said transmission points;
    determining a measured lead field matrix to define a linear matrix relationship between said injected electrical signals and said received electrical signals based on impedance between the at least one electrode of the catheter from at least one transmission point within the heart and the at least one receiving point on the torso vest at different times during a cardiac cycle and a respiratory cycle;
    calculating an inverted lead field matrix from said measured lead field matrix;
    receiving electrophysiological signals at said receiving points; and
    applying said inverted lead field matrix to said electrophysiological signals and generating a time-varying an endocardial electrical map that is without artifacts caused by the respiratory cycle due to the gating to the one point in the respiratory cycle.

12. The method according to claim 11, wherein said step of locating said receiving points comprises:
    associating said receiving points with a second location sensor; and
    reading said first location sensor and said second location sensor to determine a difference therebetween.

13. The method according to claim 11, wherein said catheter has at least two electrodes and said injecting electrical signals step is performed with different subsets of said electrodes.

14. The method according to claim 11, wherein said at least one electrode is a unipolar electrode.

15. The method according to claim 11, wherein said at least one electrode is a bipolar electrode.

16. The method according to claim 11, wherein said step of receiving said injected electrical signals is performed by determining impedances between said receiving points and subsets of said transmission points.

17. The method according to claim 11, wherein said step of receiving said injected electrical signals is performed by measuring signals produced by electrical dipoles that are generated among said subsets of said transmission points.

18. The method according to claim 11, wherein said steps of injecting electrical signals, receiving said injected electrical signals, determining a measured lead field matrix, and calculating an inverted lead field matrix are performed with respect to a predetermined phase of a respiratory cycle of said subject.

19. The method according to claim 11, wherein said steps of injecting electrical signals, receiving said injected electrical signals, determining a measured lead field matrix, and calculating an inverted lead field matrix are performed with respect to a predetermined phase of a cardiac cycle of said subject.

20. The method according to claim 11, further comprising the steps of:
    acquiring an anatomic image of a thorax of said subject;
    using said anatomic image, preparing a finite element model of said thorax having parameters, said finite element model having a calculated lead field matrix; and
    adjusting said parameters to conform said calculated lead field matrix to said measured lead field matrix.

21. The method according to claim 11, wherein said step of calculating an inverted lead field matrix comprises regularizing said measured lead field matrix.

* * * * *